United States Patent
Griffiths et al.

(10) Patent No.: US 7,666,816 B2
(45) Date of Patent: Feb. 23, 2010

(54) AGROCHEMICAL FORMULATION

(75) Inventors: Andrew John Griffiths, Bracknell (GB); Sarah Elizabeth Barnett, Bracknell (GB)

(73) Assignee: Syngenta Limited, Bracknell, Berkshire (GB)

( * ) Notice: Subject to any disclaimer, the term of this patent is extended or adjusted under 35 U.S.C. 154(b) by 202 days.

(21) Appl. No.: 10/467,744

(22) PCT Filed: Feb. 4, 2002

(86) PCT No.: PCT/GB02/00468

§ 371 (c)(1),
(2), (4) Date: Aug. 12, 2003

(87) PCT Pub. No.: WO02/063956

PCT Pub. Date: Aug. 22, 2002

(65) Prior Publication Data

US 2004/0082481 A1    Apr. 29, 2004

(30) Foreign Application Priority Data

Feb. 15, 2001    (GB) .................. 0103761.3

(51) Int. Cl.
*A01N 35/00*    (2006.01)
*A01N 25/00*    (2006.01)
*A01N 41/02*    (2006.01)
*A01N 41/12*    (2006.01)
*A01N 25/04*    (2006.01)
*A01N 25/16*    (2006.01)

(52) U.S. Cl. .............. 504/348; 504/350; 504/363; 514/788

(58) Field of Classification Search .......... 504/348, 504/350, 363; 71/64.08; 514/788, 937, 975
See application file for complete search history.

(56) References Cited

U.S. PATENT DOCUMENTS

| | | | | |
|---|---|---|---|---|
| 3,950,391 A | * | 4/1976 | Adams | 560/16 |
| 4,946,981 A | * | 8/1990 | Carter et al. | 558/415 |
| 5,283,231 A | | 2/1994 | Bell et al. | |
| 5,990,181 A | * | 11/1999 | Spyropoulos et al. | 516/118 |
| 6,710,092 B2 | * | 3/2004 | Scher et al. | 516/59 |
| 2002/0155954 A1 | * | 10/2002 | Aven | 504/348 |

FOREIGN PATENT DOCUMENTS

| | | |
|---|---|---|
| WO | 92 11254 | 7/1992 |
| WO | 95 31898 | 11/1995 |

OTHER PUBLICATIONS

Miller and Westra, Herbicide Behavior in Soils, Colorado State University, Nov. 1998 in website http://www.ext.colostate.edu/pubs/crops/00562.html.*

* cited by examiner

*Primary Examiner*—San-ming Hui
(74) *Attorney, Agent, or Firm*—William A. Teoli, Jr.

(57) ABSTRACT

An aqueous suspension concentrate formulation of insoluble or partially soluble agrochemical active ingredient in which there is used a suspending system comprising silica and an alkypolyvinylpyrrolidone is disclosed.

13 Claims, No Drawings

AGROCHEMICAL FORMULATION

"This application is a 371 filing of International Application No. PCT/GB02/00468, filed Feb. 4, 2002, the contents of which are incorporated herein by reference."

This invention relates to an agrochemical formulation and in particular to an agrochemical suspension concentrate formulation.

Agrochemicals are commonly supplied to the user as a concentrate which is subsequently diluted for application. Whilst it is possible to add an adjuvant (bioperformance enhancing additives) in the tank mix at the point of dilution, it is preferable and more convenient for the user if the additives are included in the formulation concentrate. As used herein the term "adjuvant" means a system for enhancing agrochemical bioperformance comprising one or more bioperformance enhancing additives. When the agrochemical active ingredient is insoluble or only partly soluble in water it is conveniently supplied in the form of a suspension concentrate in which finely divided solid particles of agrochemical are suspended in an aqueous formulation. It is important that the solid particles remain suspended in an aqueous formulation. It is important that the solid particles remain suspended in the concentrate formulation without significant separation over an extended period of time under the range of ambient conditions encountered in commercial practice. It is normally necessary therefore to incorporate suspending or structuring agents into the suspension concentrate. The adjuvant incorporated as bioperformance enhancing additives will not generally function to a significant or sufficient extent as a suspending or structuring agent and different agents must be used for this purpose. Indeed the present of a high loading of adjuvant in the formulation and a consequent reduction in water content of the formulation (both of which are highly desirable from efficacy and efficiency perspectives) present the formulator with major problems and in particular preclude the use of conventional suspending agents such as polysaccharide gums which require to be hydrated to be effective.

We have now found a suspending agent which is surprisingly effective even in a suspension concentrate formulation containing high levels of adjuvant and consequently reduced water levels.

Thus according to the present invention there is provided an aqueous suspension concentrate formulation of an insoluble or partially soluble agrochemical active ingredient having a concentration of adjuvant as herein defined of greater than 500 g/l characterised in that there is used a suspending system comprising silica and an alkylpolyvinylpyrrolidone.

We have additionally found that the suspending system of the present invention provides a solution to a problem encountered when the suspension concentrate is of low pH since the use of low pH further restricts the choice of suspending agents as typical agents such as bentonite are ineffective at low pH. There are a number of reasons why the suspension concentrate may be required to be of low pH and the present invention is generally applicable to all such formulations. For example, mesotrione is an agrochemical active ingredient whose solubility is highly pH dependent and which has a greatly reduced solubility at low pH. Furthermore, mesotrione exhibits a tendency to slow and long-term chemical degradation in aqueous solution and it is desirable therefore to limit the solubility by operating at low pH. Thus whilst the advantages of the present invention in terms of the ability to sustain a high loading of adjuvant are available over the full pH range, typically from about pH 9 (above which pH the silica will start to dissolve) to pH 1.5, the invention has particular advantages when the suspension concentrate has to be of low pH, for example below about pH 3.

Thus according to a further aspect of the present invention there is provided an aqueous suspension concentrate formulation of an insoluble or partially soluble agrochemical active ingredient having a pH of below pH 3, characterised in that there is used a suspending system comprising silica and an alkylpolyvinylpyrrolidone.

Whilst there is no particular lower limit of the pH of the suspension concentrate and a pH of as low as 1.5 may be viable with a suitable adjuvant system, in commercial practice it is normally desirable to avoid excessively corrosive formulations and a minimum pH of about 2.2 is normally sought. Thus, the term "low pH" as used herein means a pH of from 3 to 1.5 and preferably from 3 to 2.2, for example from about 2.2 to about 2.4.

According to a still further aspect of the present invention there is provided an aqueous suspension concentrate formulation of an insoluble or partially soluble agrochemical active ingredient having a concentration of adjuvant as herein defined of greater than 500 g/l and a pH of from 3 to 1.5 characterised in that there is used a suspending system comprising silica and an alkylpolyvinylpyrrolidone.

The alkypolyvinylpyrrolidone is a comb polymer characterised by a polyvinylpyrrolidone backbone having alkyl groups pendant therefrom. Typically one alkyl group is pendant from each vinylpyrrolidone unit, although this is not essential. The alkyl group is preferably a C4 to C30 alkyl group and specific examples of commercially available alkylpolyvinylpyrrolidones have alkyl group chain lengths of 4 and 16. The average molecular weight of the alkylpolyvinylpyrrolidone is preferably from 1,000 to 25,000 for example from 5,000 to 10,000.

The silica is preferably fumed silica and most preferably hydrophilic silica. Commercially available fumed silicas have a surface area in the range of from 50 $m^2/g$ to 380 $m^2/g$ and a mean primary particle size from 7-50nm. Preferably the fumed silica has a surface area of greater than 100 $m^2/g$, for example from 150 to 380 $m^2/g$. Preferably the fumed silica has a mean primary particle size below 20 nm, for example from 7 to 20 nm.

It is believed that the system is structured by the interaction of the alkylpolyvinylpyrrolidone and silica. We have found that the structuring of the suspension concentrates of the present invention provides excellent stability, even when the suspension concentrate undergoes shear forces, for example on mixing. In commercial practice, it is desirable for a suspension concentrate to have a maximum separation of 20% and preferably not more than 15% of an accelerated test over 8 weeks at 40° C. where the stability index (% separation) is as defined in the Examples. An ideal composition has no more than 2% separation.

The nature of the adjuvant is not critical to the invention and those skilled in the art will be able to select suitable adjuvant systems to optimise the bioperformance of the active ingredient concerned. A wide range of adjuvant types is available to those skilled in the art and whilst it is not intended to supply a comprehensive list, typically the adjuvant system may for example comprise one or more enhancers such as ethylene oxide/propylene oxide block copolymers, alcohol ethoxylates (such as Brij 97 and Brij 93), alkyl polysaccharides (such as Atplus 435™), alkyl phenyl ethoxylates (such as Agral 90™), polyethoxylated nonyl phenyl ether carboxylic acid (such as Sandopan MA-18), tallow amine ethoxylates, oil based derivatives (either mineral or vegetable) (such as Atplus 411F™ and Atplus 463™), sorbitol, ethoxylated Sorbitan derivatives (such as one of the Tween™ series of surfactants), acetylenic diol derivatives (such as one of the Surfynol series) and polyethyleneglycol. The bioperformance may additionally be enhanced by the inclusion in the formulation of one or more wetting agents such as short chain alcohol ethoxylates.

In one aspect of the present invention, the concentration of adjuvant (i.e. the total concentration of bioperformance enhancing additives) is greater than 500 g/l. In order to achieve maximum enhancement of the activity of the active ingredient, it may be desired that the adjuvant concentration is greater than about 650 g/l. The higher the adjuvant concentration that is added in order to provide the desired bioperformance enhancement, the more difficult it becomes to achieve a stable suspension concentrate. The benefits of the present invention are therefore most apparent at higher adjuvant concentrations. The upper limit of the adjuvant concentration will be set by practical considerations such as the fact that increasing the adjuvant content reduces the water content in the suspension concentrate. An effective suspension concentrate should have a minimum of about 5% water.

It is believed that the structuring of the suspension concentrate of the present invention is achieved by the interaction of the alkylpolyvinylpyrrolidone and silica. The concentration of alkylpolyvinylpyrrolidone is preferably from 5 to 30 g/l and more preferably from 10 to 30 g/l. Higher concentrations of alkylpolyvinylpyrrolidone may be used if desired and are within the scope of the present invention, but we have found that increasing the concentration of alkylpolyvinylpyrrolidone above the preferred levels may provide little if any additional stabilisation and may in some circumstances even reduce the stability. When mesotrione is the active ingredient for example, a concentration of alkylpolyvinylpyrrolidone of from 10 to 20 g/l is especially preferred.

Increasing the content of silica increases the degree of structuring but at the same time increases the viscosity of the composition. Thus a minimum of about 10 g/l silica is required to provide effective structuring whilst a concentration about 40 g/l is likely to yield a composition which is too viscous for practical purposes. The concentration of silica is preferably from 20 to 35 g/l.

The exact concentrations of alkylpolyvinylpyrrolidone and silica used will depend on the nature and concentrations of all other components, including water, in the formulation. Therefore, the ranges given above are by way of example only and the use of a concentration outside these ranges is still within the scope of the invention.

As noted above, whilst the suspension concentrate of the present invention may be applied to a wide range of insoluble active ingredients (that is to say active ingredients whose solubility in water is such that a significant solid content exists in the concentrate), it is especially applicable to suspension concentrates which either contain a high loading of adjuvant, or involve an active ingredient which requires formulation at low pH, or both. The concentration of the active ingredient in the suspension concentrate is not critical for the purposes of the present invention but will typically be from 50 g/l to 500 g/l for example from 75 g/l to 250 g/l. As examples of such active ingredients there may be mentioned mesotrione or sulcotrione. When the active ingredient is mesotrione or sulcotrione, the concentrate formulation of the invention is particularly suitably for use as an herbicide.

It will normally be necessary to acidify the suspension concentrate to achieve the desired low pH. Any suitable acidifying agent may be used but we have found that phosphoric acid is particularly useful as it provides excellent control over the formulation pH. With certain active ingredients such as mesotrione, phosphoric acid provides an internal buffer system.

In achieving the most suitable balance between increasing the structuring effect of the silica/alkylpolyvinylpyrrolidone interaction whilst avoiding excessive formulation viscosity, it may be desirable to add a viscosity modifying agent. Numerous viscosity modifying agents are known to those skilled in the art and typical examples include ethers such as dipropylene glycol dimethyl-ether and tripropyleneglycol-n-butyl ether, optionally ethoxylated $C_{6\ to\ 10}$ alcohols such as n-octanol, 2-ethylhexanol and 3-butoxypropan-2-ol and glycols such as propylene glycol diacetate. We have found that n-octanol is an inexpensive and effective viscosity modifying agent which can even produce some additional beneficial effects such as an element of bioperformance enhancement. The viscosity modifying agent can be present in a concentration of from 0 to 250 g/l, for example from 50 to 150 g/l.

Other additives which are typically present in suspension concentrates can also be included. In commercial suspension concentrates it is often preferred for example to include an anti-foam and we have found that silicone anti-foam agents are especially suitable for incorporation in the suspension concentrate of the present invention. The anti-foam is typically present at a concentration of from 0.5 to 5 g/l, for example from 0.5 to 2 g/l.

In milling the solid active ingredient to form the suspension concentrate it may be desirable to add a dispersing agent to stabilise the initial suspension. Typical of such dispersing agents is an ethylene oxide/propylene oxide block copolymer of molecular weight 3000, containing approximately 50% hydrophobe by weight. Such dispersing agents can be added if desired but are not believed to be essential to the formation of an effective suspension concentrate since the interaction of the alkylpolyvinylpyrrolidone and silica provide effective structuring. Typically the dispersing agent may be present at a concentration of from 0 to 20 g/l.

The suspension concentrate is conveniently prepared by milling of technical wet paste of the agrochemical active ingredient in the presence of the other components of the composition. The order of addition of the components is not critical although it is preferable for the alkypolyvinylpyrrolidone and the silica to be present prior to the milling such that the structuring of the composition takes place during and immediately following milling. It is and advantage of the composition of the present invention that the structuring effect resulting from the interaction of the silica and the alkypolyvinylpyrrolidone rapidly recovers following the application of shear forces during milling such that any tendency for the milled solid active ingredient to undergo aggregation is reduced. It is convenient to add one of either silica or the alkpolyvinylpyrrolidone after all the other components have been added (but before milling) so that the structuring of the composition only takes place once the components are homogenised. Acidification of the suspension concentrate to the desired pH may take place if desired before the milling but conveniently takes place after.

EXAMPLES

The invention is illustrated by the following Examples in which all parts and percentages are by weight unless otherwise stated.

The description of the products used in the Examples is as follows:

| Component | Description |
|---|---|
| TWEEN 20 (TWEEN is a trademark of Uniqema) | Ethoxylated (20)-sorbitan monolaurate |
| RHODASURF DA630E (RHODASURF is a trademark of Rhodia) | Ethoxylated (6)-isodecyl alcohol |
| PLURONIC PE10500 (PLURONIC is a trademark of BASF) | Polyethylene oxide-polypropylene oxide Polyethylene oxide block copolymer |
| AGRIMER AL-22 (AGRIMER is a trademark of ISP) | Alkylated polyvinylpyrrolidone |

-continued

| Component | Description |
|---|---|
| AEROSIL 300 (AEROSIL is a trademark of Degussa) | Hydrophilic fumed silica |

Example 1

Suspension concentrates of mesotrione were prepared by the following general method:

The adjuvant (as herein defined) and the viscosity modifying agent (if used) was weighed into a vessel and homogenised. The dispersing agent for mesotrione (if used) is typically a solid ethylene oxide/propylene oxide block copolymer which is conveniently warmed to its melting point (typically 35° C. to 60° C. depending on the exact nature of the product) and added in the molten state while stirring. The alkylpolyvinylpyrrolidone was then added and mixing was continued until a homogeneous product was obtained. The desired quantity of water was then added and mixed in together with the antifoam (if used).

Mesotrione technical wet paste was added and a higher mixing speed was initiated and continued until homogenous suspension was obtained. Fumed silica was then weighed into the vessel, wetted into the formulation using moderate speed on the mixer and then mixing was completed using a higher speed. A homogeneous, smooth, mobile and viscous liquid was produced. This premix was milled using an "Eiger" mini motor mill to achieve a particle size of 100% less than 50 µm and greater than 70% less than 5 µm as measured using a "Malvern" Mastersizer S.

The resulting millbase was adjusted to pH 2.2 to 2.4 at 20° C. using orthophosphoric acid (85.5% w/w) and the suspension concentrate was mixed for approximately 5 minutes, using a paddle stirrer to achieve effective mixing. The stability of the composition was evaluated as described below.

Compositions prepared using the above general method are given in Table 1.

The stability of each suspension concentrate composition was measured in an accelerated test as follows:

The suspension concentrate was poured into a graduated glass cylinder which was maintained at the test temperature (25° C.). Instability (phase separation) is indicated by the appearance of a clear layer at the top of the cylinder. The stability index (percentage separation) is recorded as % clear layer (height of clear layer divided by total height of formulation multiplied by 100).

It will be appreciated that the lower the stability index, the more stable is the composition. It should be noted that these accelerated tests represent very severe conditions and it is estimated that 16 weeks at 40° C. corresponds to more than four years under normal ambient conditions. The results are presented for the 16 week storage test at 25° C. in Table 2 below.

TABLE 2

16 Week Storage Test at 25° C.

| | Example No | | | | | | | | | |
|---|---|---|---|---|---|---|---|---|---|---|
| | 1 | 2 | 3 | 4 | 5 | 6 | 8 | 9 | 10 | 11 |
| Stability Index (% clear layer) | 1.5 | 1.00 | 0.5 | 1.5 | 1.5 | 1.0 | 0.5 | 1.0 | 1.0 | 0.5 |

The invention claimed is:

1. An aqueous suspension concentrate formulation having a pH of from 3 to 1.5 comprising (i) an insoluble or partially soluble agrochemical active ingredient, (ii) an adjuvant for enhancing agrochemical bioperformance comprising one or more bioperformance enhancing additives, said adjuvant having a concentration of greater than 500 g/l, and (iii) a suspending system comprising from 10 to 40 g/l silica and from 5 to 30 g/l of an alkylpolyvinylpyrrolidone.

2. An aqueous suspension concentrate formulation according to claim 1, having a pH of below pH 3.

3. An aqueous suspension concentrate formulation according to claim 1, wherein the alkyl group in the alkylpolyvinylpyrrolidone is a $C_4$ to $C_{30}$ alkyl group.

4. An aqueous suspension concentrate formulation according to claim 1, wherein the average molecular weight of the alkylpolyvinylpyrrolidone is from 1,000 to 25,000.

TABLE 1

| Component | Concentration (g/l) | Example Number | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Mesotrione | | 100 | 100 | 100 | 100 | 100 | 100 | 100 | 100 | 100 | 100 | 100 |
| TWEEN 20 | | 490.5 | 490.5 | 490.5 | 490.5 | 490.5 | 490.5 | 490.5 | 490.5 | 490.5 | 490.5 | 490.5 |
| RHODASURF DA630E | | 218 | 218 | 218 | 218 | 218 | 218 | 218 | 218 | 218 | 218 | 218 |
| PLURONIC PE10500 | | 16.4 | 16.4 | 16.4 | 16.4 | 16.4 | 16.4 | 16.4 | 16.4 | 16.4 | 16.4 | 16.4 |
| AGRIMER AL-22 | | 16.4 | 19.6 | 16.4 | 27.3 | 16.4 | 19.6 | 19.6 | 16.4 | 24.0 | 16.4 | 16.4 |
| AEROSIL 300 | | 26.2 | 32.7 | 32.7 | 32.7 | 29.4 | 29.4 | 29.4 | 32.7 | 32.7 | 26.2 | 26.2 |
| Octan-1-ol | | 87.2 | 87.2 | 54.5 | 87.2 | 87.2 | 54.5 | 87.2 | 87.2 | 87.2 | 87.2 | 87.2 |
| Phosphoric acid (85.5% w/w) | | 24.5 | 24.5 | 24.5 | 24.5 | 24.5 | 24.5 | 24.5 | 24.5 | 24.5 | 24.5 | 24.5 |
| Antifoam MSA | | 1 | 1 | 1 | 1 | 1 | 1 | 1 | 1 | 1 | 1 | 1 |
| Water | | To 1 Liter | To 1 Liter | To 1 Liter | To 1 Liter | To 1 Liter | To 1 Liter | To 1 Liter | To 1 Liter | To 1 Liter | To 1 Liter | TO 1 Liter |

5. An aqueous suspension concentrate formulation according to claim 1, wherein the concentration of alkylpolyvinylpyrrolidone is from 5 to 30 g/l.

6. An aqueous suspension concentrate formulation according to claim 1, wherein the silica is fumed silica.

7. An aqueous suspension concentrate formulation according to claim 6, wherein the fumed silica has a surface area of greater than 100 m$^2$/g.

8. An aqueous suspension concentrate formulation according to claim 6, wherein the fumed silica has a mean primary particle size below 20 nm.

9. An aqueous suspension concentrate formulation according to claim 1, wherein the concentration of silica is from 10 to 40 g/l.

10. An aqueous suspension concentrate formulation according to claim 1, wherein the adjuvant concentration is greater than about 650 g/l.

11. An aqueous suspension concentrate formulation according to claim 1, wherein the suspension concentrate has a minimum of about 5% water.

12. An aqueous suspension concentrate formulation according to claim 1, wherein the agrochemical active ingredient is mesotrione or sulcotrione.

13. An aqueous suspension concentrate formulation according to claim 12, wherein the agrochemical active ingredient is mesotrione.

* * * * *